United States Patent [19]

Noone

[11] Patent Number: 5,427,116

[45] Date of Patent: Jun. 27, 1995

[54] DEVICE FOR MAINTAINING A DESIRED LOAD ON A JOINT DURING OBSERVATION UNDER MAGNETIC RESONANCE IMAGING

[75] Inventor: Michael Noone, Chapel Hill, N.C.

[73] Assignee: William Vanarthos, Lexington, Ky.

[21] Appl. No.: 91,575

[22] Filed: Jul. 13, 1993

[51] Int. Cl.⁶ .............................................. A61B 5/103
[52] U.S. Cl. .................................. 128/774; 128/653.5; 128/779
[58] Field of Search ................... 128/653.2, 653.5, 774, 128/779, 782; 73/379.3; 33/512

[56] References Cited

U.S. PATENT DOCUMENTS

| | | |
|---|---|---|
| 2,087,584 | 7/1937 | Staudinger . |
| 3,680,386 | 8/1972 | Cannon . |
| 3,690,308 | 9/1972 | Daniels . |
| 3,752,144 | 8/1973 | Weigle, Jr. . |
| 4,159,640 | 7/1979 | Lévêque et al. . |
| 4,201,226 | 5/1980 | Phillips . |
| 4,323,080 | 4/1982 | Melhart . |
| 4,534,364 | 8/1985 | Lamoreux . |
| 4,883,066 | 11/1989 | Widdoes et al. ..................... 128/774 |
| 4,969,471 | 11/1990 | Daniel et al. . |
| 5,014,719 | 5/1991 | McLeod . |
| 5,085,226 | 2/1992 | DeLuca et al. ....................... 128/774 |

Primary Examiner—Ruth S. Smith
Attorney, Agent, or Firm—Kenyon & Kenyon

[57] ABSTRACT

A medical device for use in conjunction with magnetic resonance imaging includes a frame which is selectively coupleable to a surface for supporting a patient, and a receiving member for receiving a body member of the patient, usually a hand or a foot of the patient. The receiving member is coupled to the frame such that the it may move relative to the frame along an axis. A moveable member is also coupled to the frame such that it may move relative to the frame along the axis and a spring member is coupled between the moveable member and the receiving member so that the displacement of the moveable member relative to the receiving member is proportional to a component of a force exerted against the receiving member in a direction parallel to the axis. An indicator for indicates the force applied to the receiving member and, consequently, to the joint. All of the elements of the device are comprised of non-magnetic materials.

14 Claims, 4 Drawing Sheets

DEVICE FOR MAINTAINING A DESIRED LOAD ON A JOINT DURING OBSERVATION UNDER MAGNETIC RESONANCE IMAGING

FIELD OF THE INVENTION

The present invention relates generally to orthopedic devices and is more specifically related to orthopedic devices for use in conjunction with Magnetic Resonance Imaging.

BACKGROUND OF THE INVENTION

Magnetic Resonance (MRI) Imaging, or Nuclear Magnetic Resonance (NMR) Imaging, has enabled doctors to obtain cross-sectional images of the various structures of the human body with greater contrast between tissues than is commonly available with current x-ray techniques. In addition, three-dimensional images of body structures may be created from MRI images.

The enhanced contrast between tissues and the ability to create three-dimensional images of body structures from MRI images has resulted in an increasing dependence on MRI in the diagnosis and treatment of various illnesses and injuries. MRI has proven extremely useful in the diagnosis and treatment of injuries to the joints. Since a large percentage of the debilitating sports injuries that are treated are to the knee and the shoulder, MRI has been most frequently employed in imaging these joints. However, it is also commonly used to evaluate the wrist, elbow, ankle and hip.

During imaging, the force on a joint is unknown to the radiologist analyzing the image. But, even if known the force on the joint could vary during the imaging process. Consequently, these factors could result in an inaccurate or incomplete analysis of the images obtained.

SUMMARY OF THE INVENTION

Thus, the present invention is directed to a medical device for use in conjunction with magnetic resonance imaging including a frame which may be selectively coupled to a surface for supporting a patient and a receiving member for receiving a body member of the patient. This is usually the patient's hand or foot depending upon whether the user wishes to observe the patient's upper or lower extremity. The receiving member is coupled to the frame such that the receiving member may move relative to the frame along an axis. The device also includes a plurality of spring members coupled between the frame and the receiving member so that the displacement of the receiving member relative to the frame, when a force is applied to the receiving member, is proportional to a component of the force which is exerted against the receiving member in a direction parallel to the axis. An indicator for indicates the force applied to the receiving member. In addition, all of the elements of the device which, when in an operative position, are located within a predetermined area are comprised of non-ferromagnetic materials.

In addition, a device according to the present invention may also include means for providing a lateral stress on a joint during magnetic resonance imaging.

DETAILED DESCRIPTION

Figure 1:
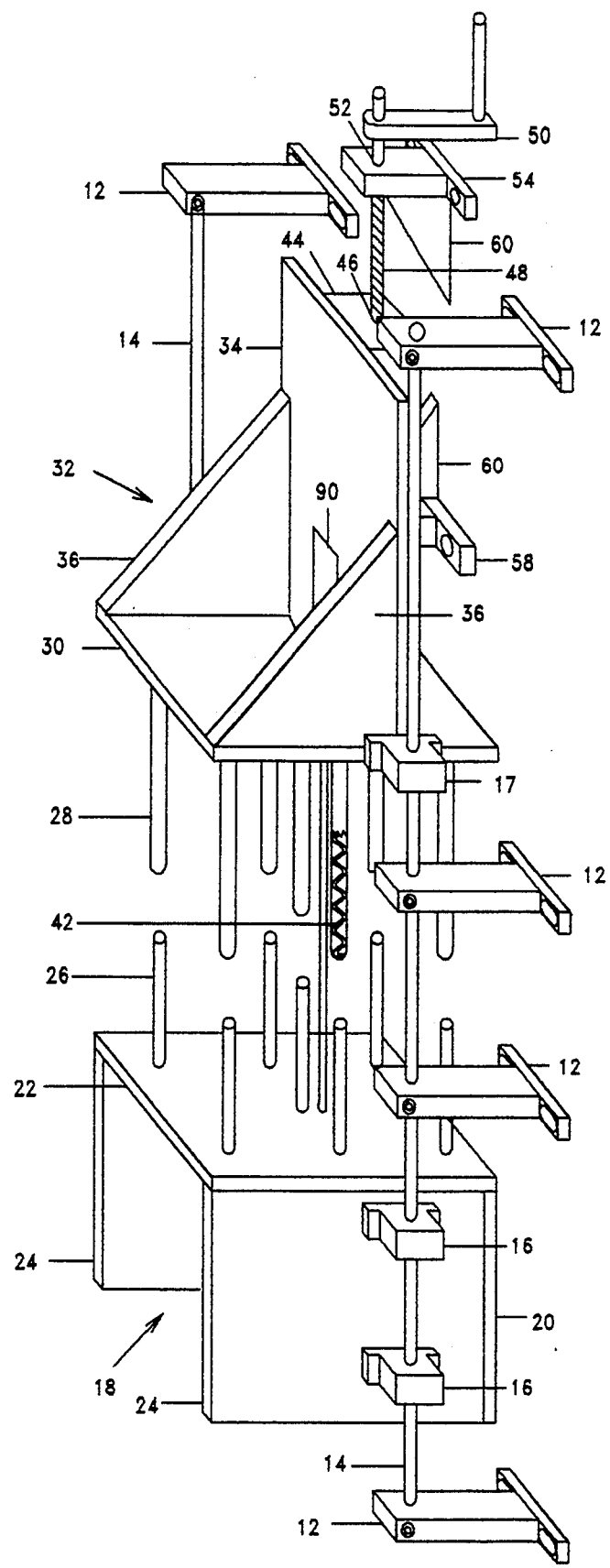
FIG. 1 shows a side elevation view of a device according to a first embodiment of the present invention.

Referring to FIG. 1, a device according to the present invention is indicated generally by the numeral 10. The device 10 includes a plurality of mounting plates 12 which may be coupled to a surface on which a patient is supported during magnetic resonance imaging. The mounting plates 12 are arranged in a line on one side of the device 10 while a second plurality of mounting plates 12' are arranged in a line parallel to the first line of mounting plates 12 on the opposite side of the device 10. Each of the mounting plates 12 and 12' may preferably be made of acetal. A connecting bar 14 is coupled between the mounting plates 12 while a connecting bar 14' is coupled between the mounting plates 12'. Two anchoring members 16 are slidably received on the connecting bar 14 and a third anchoring member 17 is slidably received on the connecting bar 14. In addition, two anchoring members 16' are slidably received on the connecting bar 14' and a third anchoring member 17' is slidably received on the connecting bar 14'. The anchoring members 16 and the anchoring members 16' are coupled to a receiving structure 18. Each of the anchoring members 16, 16', 17 and 17' may be made of ultra-high molecular weight polyethylene (UHMWPE).

The receiving structure 18, which is slidably mounted on the connecting bars 14 and 14', is a box-like structure composed of a bottom plate 20, a rearward plate 22 and two side plates 24. The bottom plate 20, the rearward plate 22 and each of the side plates 24 are preferably made of acrylic. An upper surface and a forward surface of the receiving structure 18 are open. A plurality of cylindrical projections 26 which are preferably made of acetal extend from the rearward plate 22 in a direction substantially parallel to the connecting bars 14 and 14'. Each of these cylindrical projections 26 is received within one of a corresponding plurality of tubular structures 28 which are preferably made of acetal. Each of the tubular structures 28 projects from a forward plate 30, which may preferably be made of acrylic, of a moveable support structure 32 in a direction substantially parallel to the connecting bars 14 and 14'. In addition, a rod 38 projects from the rearward plate 22 in a direction substantially parallel to the connecting bars 14 and 14' and extends through a hole 40 formed in the forward plate 30.

Figure 2:
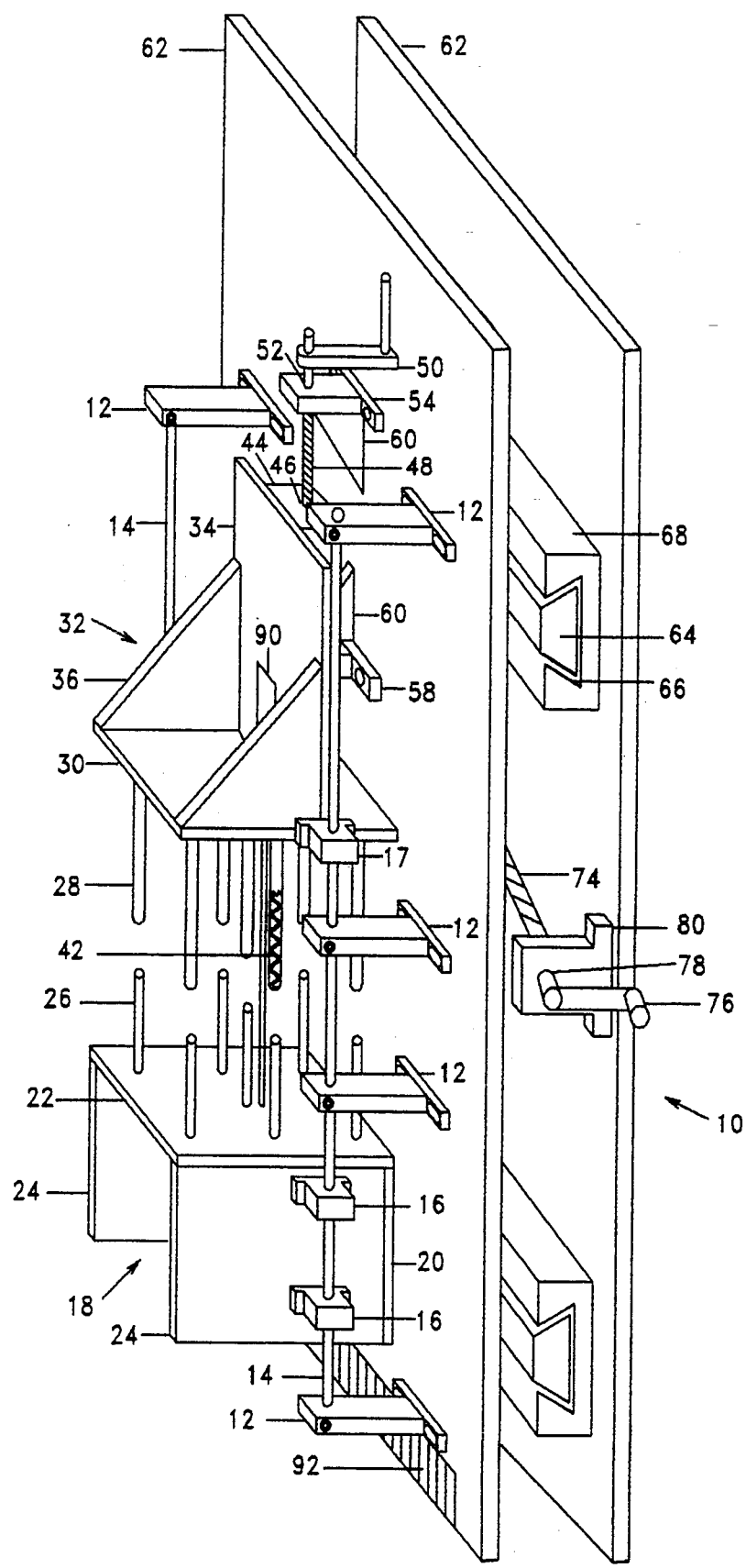
FIG. 2 shows a side perspective view of a device according to a second embodiment of the present invention.

The rear support structure 32 preferably includes two triangular side plates 36 and a base plate 34. The triangular side plates 36 and the base plate 34 are preferably made of acrylic. The base plate 34 or the rod 38 may be marked to indicate the extent of the penetration of the rod 38 through the hole 40. Also, as seen in FIG. 2, each tubular structure 28 is adapted to receive a spring 42 for abutting an end surface of a corresponding cylindrical projection 26. Each spring 42 is made of a non-ferromagnetic material which is preferably beryllium copper. The rear support structure 22 is slidably coupled to the connecting bars 14 and 14' by means of anchoring members 17 and 17', respectively. A plate 44, which is preferably made of acetal, projects downward from the rearward end of the base plate 34 and includes a threaded bore 46 which receives a threaded rod 48 which is preferably a stainless steel leadscrew. The threaded rod 48 is coupled at one end to a crank arm 50 and extends through a bore 52 in a mounting bar 54, through the threaded bore 46, to a bore in a bracket 58 which is preferably made of UHMWPE. The mounting bar 54 and the bracket 58 are coupled to the surface on which the patient is supported during magnetic resonance imaging. The bracket 58 is supported by a triangular brace 60 which is also coupled to the surface on which the patient is supported during magnetic resonance imaging. The triangular brace 60 may preferably be made of acrylic.

Those skilled in the art will recognize that, as the device shown in FIG. 1 includes 7 tubular structures 28, it may include up to 7 springs. Thus, a user may achieve a desired force on the joint, relative to a given displacement of the support structure 32, by increasing or decreasing the number of springs received in the tubular structures 28 and by employing springs of various spring constants. Those skilled in the art will also recognize that any number of cylindrical projections 26 and tubular structures 28 may be provided so that a different number of springs and, consequently, a greater number of total equivalent spring constants may be achieved.

In operation, the user first inserts a number of springs into the tubular structures 28 until a desired total equivalent spring constant is achieved. The device 10 is then aligned and coupled to the support surface, i.e., the mounting plates 12 and 12', the mounting bar 54, the bracket 58 and the brace 60 are coupled to the support surface and the receiving structure 18 is aligned so that each of the cylindrical projections 26 is received within a corresponding tubular structure 28. The patient is then positioned on the support surface and his foot is placed in the receiving structure 18 so that it abuts the rearward plate 22 and the patient is secured to the support surface so that his leg may not move relative to the device 10. The user then turns the crank arm 50 so that the threaded rod 48 rotates within the threaded bore 46 thereby moving the rear support structure 32 forward until a desired displacement and, consequently, a desired force on the knee, as indicated by the rod 38, is achieved. The threaded rod 48 prevents further motion of the rear support structure 32 until the user turns the crank arm 50 to release the force from the patient's knee.

The displacement required to achieve a desired force on a joint may be quickly calculated through the use of a series of cards each being calibrated to the total equivalent spring constant selected by the user to correspond to the number and the spring constant of the springs employed. A card corresponding to the selected total equivalent spring constant and indicating the current force on the knee may be placed under the rod 38 when the device 10 is being set up.

Figure 3:
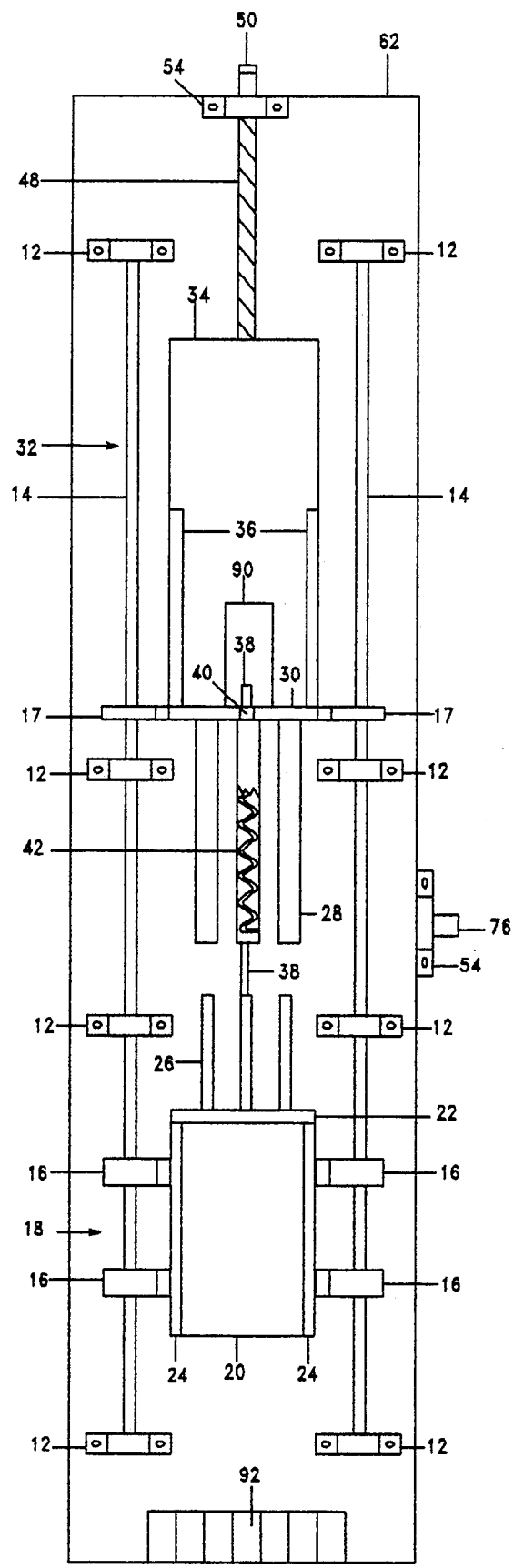
FIG. 3 shows a top view of a device according to the second embodiment of the present invention.
Figure 4:
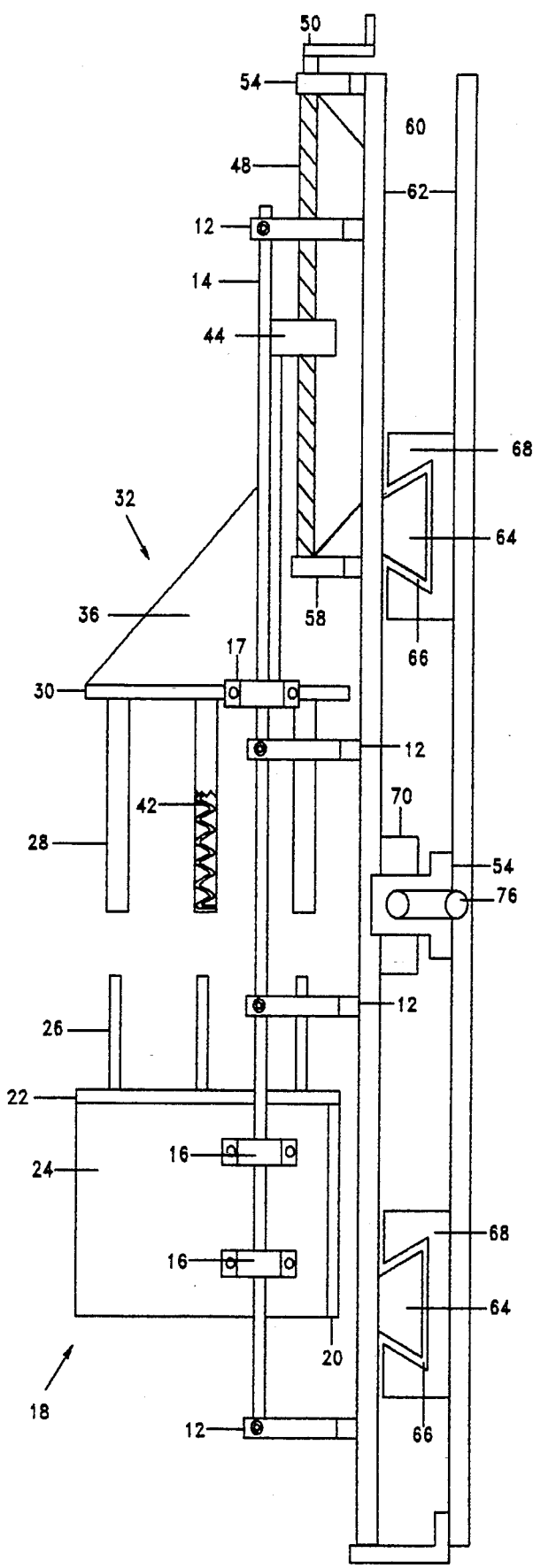
FIG. 4 shows a side view of a device according to the second embodiment of the present invention.

As shown in FIGS. 2-4, a device 10' according to a second embodiment of the invention may, in addition to stressing a joint in an axial direction, include an apparatus for providing a lateral stress to a joint during magnetic resonance imaging. Those skilled in the art will understand that the term "axial direction" in regard to this device refers to a direction substantially parallel to the limb of which the joint is a part when the limb is fully extended. The term lateral refers to a direction substantially perpendicular to the axial direction. The device 10' is constructed in accord with the description of the first embodiment except that the mounting plates 12 and 12' of this embodiment are coupled to a moveable surface 62. The moveable surface 62 is mounted on bars 64 which ride in slots 66 formed in brackets 68. The brackets 68 are preferably mounted to the surface on which the patient is supported so that the slots 66 are oriented substantially perpendicular to the connecting bars 14 and 14'. A plate 70, which is preferably made of acetal, projects downward from the moveable surface 62 and includes a threaded bore which receives a threaded rod 74 which is preferably a leadscrew. The threaded rod 74 is coupled at one end to a crank arm 76 and extends through a bore 78 in a mounting bar 80, through the threaded bore 72, to a bore in a bracket which is preferably made of UHMWPE. The mounting bar 80 and this bracket are coupled to the surface on which the patient is supported during magnetic resonance imaging. This bracket may also be supported by a triangular brace coupled to the surface on which the patient is supported during magnetic resonance imaging. The triangular brace may also be made of acrylic.

In operation, the user first inserts a number of springs into the tubular structures 28 until a desired total equivalent spring constant is achieved. The device 10' is then aligned and coupled to the moveable surface 62, i.e., the mounting plates 12 and 12', the mounting bar 54, the bracket 58 and the brace 60 are coupled to the moveable surface 62 and the receiving structure 18 is aligned so that each of the cylindrical projections 26 is received within a corresponding tubular structure 28. The moveable surface 62 is then placed in a rest position. At this point, the user may place a card 90, calibrated for the total equivalent spring constant which the user has chosen, beneath the rod 38 on the base plate 34. The patient is then positioned on the support surface and his foot is placed in the receiving structure 18 so that it abuts the rearward plate 22 and the patient is secured to the support surface so that his leg may not move relative to the device 10'. The user then turns the crank arm 50 so that the threaded rod 48 rotates within the threaded bore 46 thereby moving the rear support structure 32 forward until a desired axial displacement and, consequently, a desired axial force on the knee, as indicated by the position of the rod 38 over the card 90, is achieved. The threaded rod 48 prevents further motion of the rear support structure 32 until the user turns the crank arm 50 to release the force from the patient's knee. Thereafter, the user turns the crank arm 76 until a desired displacement of the moveable surface from the rest position and, consequently, a desired displacement of the patient's foot relative to the patient's knee, as indicated on the scale 92, is achieved. The device 10' maintains this displacement, and the lateral force resulting from the displacement until the user turns the crank arm 76 to relieve the lateral displacement. Thus, the patient's knee may be observed under magnetic resonance imaging under carefully controlled conditions.

Those skilled in the art will recognize that, although the operation of the various embodiments of this device has been described in regard to the imaging of a patient's knee, a patient's elbow may be examined by simply placing the patient's hand in the receiving structure 18 so that it abuts the rearward plate 22 and thereafter immobilizing the patient's arm relative to the device 10 or 10'. Further, those skilled in the art will recognize that other points on the body may also be subjected to known axial force or lateral displacements through the teaching of this invention and such use is considered within the scope of this invention which is intended to be limited only by the scope of the claims appended hereto.

What is claimed is:

1. A medical device for use in conjunction with magnetic resonance imaging comprising:
   a frame comprised of non-ferromagnetic material, the frame including means for selectively coupling the frame to a surface for supporting a portion of the body of a patient;
   a receiving member formed of non-ferromagnetic material for receiving a body member of the patient, the receiving member being coupled to the frame such that the receiving member may move relative to the frame along an axis;
   a moveable member formed of non-ferromagnetic material, the moveable member being coupled to the frame such that the moveable member may move relative to the frame along the axis;
   a spring formed of non-ferromagnetic material coupled between the moveable member and the receiving member for providing resistance to the movement of the moveable member relative to the receiving member so that the displacement of the moveable member relative to the receiving member, when the position of the receiving member is maintained, is proportional to a component of a force applied to the receiving member in a direction parallel to the axis; and
   an indicator formed of non-ferromagnetic material, coupled to the frame for indicating the force applied to the receiving member.

2. A device according to claim 1, wherein the spring is a beryllium spring.

3. A medical device for use in conjunction with magnetic resonance imaging comprising:
   a frame of non-ferromagnetic material including means for selectively coupling the frame to a surface for supporting a portion of the body of a patient;
   a receiving member formed of non-ferromagnetic material for receiving a body member of the patient, the receiving member being nonrotatably coupled to the frame such that the receiving member may move relative to the frame only along an axis;
   at least one linking member formed of non-ferromagnetic material, the linking member being coupled between the frame and the receiving member so that, when a force is applied to the receiving member in a direction parallel to the axis the receiving member moves relative to the frame; and
   an indicator coupled to the frame for indicating the distance the receiving member has moved relative to the frame.

4. A device according to claim 3, further including means for moving the receiving member a predetermined distance in a direction substantially perpendicular to the axis when a body member of the patient is received in the receiving member, 5. A medical device for use in conjunction with magnetic resonance imaging comprising:
   a frame of non-ferromagnetic material including means for selectively coupling the frame to a surface for supporting a portion of the body of a patient;
   a receiving member formed of non-ferromagnetic material for receiving a body member of the patient, the receiving member being nonrotatably coupled to the frame such that the receiving member may move relative to the frame only along an axis;
   a plurality of first housings coupled to the receiving member;
   a support member of non-ferromagnetic material coupled to the frame so that the support member may move, relative to the frame, along the axis;
   a plurality of second housings coupled to the support member, each second housing being formed of non-ferromagnetic material and including a bore, wherein each bore slidably receives a corresponding first housing;
   a spring coupled between one of the first housings and a corresponding second housing;
   means for indicating the displacement of the receiving member relative to the support member.

6. A device according to claim 5, further comprising means for exerting a stress on the body member, wherein the stress is oriented laterally relative to the axis.

7. A device for applying a desired loading to a selected portion of the body of a patient during observation under magnetic resonance imaging, the device comprising:
   a frame;
   an abutting surface for pressing against the selected portion of the patient's body, wherein the patient's body is maintained in a substantially horizontal position and the selected portion of the patient's body is maintained in a position which is fixed relative to the frame so that the abutting surface is immobilized relative to the frame;
   means for applying a predetermined force to the abutting surface along the axis so that the selected portion of the patient's body is loaded along the axis with the predetermined force,
   wherein all of the components of the device are constructed of non-ferromagnetic materials.

8. A device according to claim 7, wherein the means for applying a predetermined force includes a first spring and a moveable member movably coupled to the frame, wherein the spring is coupled between the moveable member and the abutting surface so that, as the moveable member is moved relative to the abutting surface, a force is exerted on the abutting surface by the first spring.

9. A device according to claim 8, wherein the means for applying a predetermined force includes a plurality of second springs coupled between the moveable member and the abutting surface so that, as the moveable member is moved relative to the abutting surface, a force is exerted on the abutting surface by the second springs.

10. A device according to claim 8, wherein the spring is a beryllium spring.

11. A device according to claim 8, further comprising a locking device for maintaining the position of the moveable member relative to the abutting surface when the desired force is applied.

12. A device according to claim 8, further comprising an indicator coupled to the frame for indicating the displacement of the moveable member relative to the support surface.

13. A device according to claim 7, further comprising a clamp coupled to the frame for securing the device to a surface for supporting a portion of the body of the patient.

14. A medical device for use in conjunction with magnetic resonance imaging comprising:

a frame formed of a non-ferromagnetic material;

a non-ferromagnetic receiving member for receiving a body member of the patient, the receiving member being coupled to the frame such that the receiving member may move relative to the frame along an axis;

a non-ferromagnetic moveable member coupled to the frame such that the moveable member may move relative to the frame along the axis;

a non-ferromagnetic spring coupled between the moveable member and the receiving member for providing resistance to the movement of the moveable member relative to the receiving member so that the displacement of the moveable member relative to the receiving member, when the position of the receiving member is maintained, is proportional to a component of a force applied to the receiving member in a direction parallel to the axis.

* * * * *